United States Patent [19]

Chibata et al.

[11] 4,438,044
[45] Mar. 20, 1984

[54] DI-L-CYSTEINE L-MALATE AND PROCESS FOR THE PRODUCTION THEREOF

[75] Inventors: Ichiro Chibata, Suita; Akihiko Sumi, Ashiya; Osamu Ohtsuki, Nagaokakyo; Nozomu Izutsu, Yao, all of Japan

[73] Assignee: Tanabe Seiyaku Co., Ltd., Japan

[21] Appl. No.: 284,119

[22] Filed: Jul. 16, 1981

[30] Foreign Application Priority Data

Jul. 31, 1980 [JP] Japan ................................ 55-106280

[51] Int. Cl.$^3$ .............................................. C07C 51/02
[52] U.S. Cl. ................................. 260/501.12; 424/319
[58] Field of Search ..................... 260/501.12; 562/556

[56] References Cited

PUBLICATIONS

Pine et al, Jour. Amer. Chem. Soc. vol. 77 (1955) 3153–3154.

*Primary Examiner*—Bernard Helfin
*Attorney, Agent, or Firm*—Jordan B. Bierman; Linda Bierman

[57] ABSTRACT

Novel di-L-cysteine L-malate of the formula:

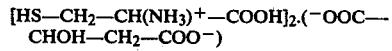

[HS—CH$_2$—CH(NH$_3$)$^+$—COOH]$_2$.($^-$OOC—CHOH—CH$_2$—COO$^-$)

which has excellent storage stability and excellent pharmacological activities and is useful for the preparation of the amino acid infusion solutions, and process for the preparation of the di-L-cysteine L-malate by reacting 2 moles of L-cysteine L-malate and more than 0.9 mole of L-malic acid in an aqueous medium and collecting the resulting crystalline di-L-cysteine L-malate.

9 Claims, 3 Drawing Figures

DI-L-CYSTEINE L-MALATE AND PROCESS FOR THE PRODUCTION THEREOF

The present invention relates to di-L-cysteine L-malate of the formula:

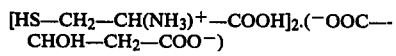

[HS—$CH_2$—CH($NH_3$)$^+$—COOH]$_2$.($^-$OOC—CHOH—$CH_2$—COO$^-$)  [I]

and a process for the production thereof.

It is well known that L-cysteine shows important physiological effects on liver function and skin metabolism. L-cysteine is industrially obtained by reduction of L-cysteine by electrolytic methods. The crystalline L-cysteine is unfavorably easily oxidized with oxygen in air, and hence, the L-cysteine is usually handled in the form of hydrochloride in order to enhance the storage stability of L-cysteine. Nevertheless, the L-cysteine hydrochloride shows still inferior storage stability because it is decomposed and releases hydrochloric acid during storage. Moreover, the hydrochloride is not preferable for the preparation of a crystalline amino acid infusion solution which has recently rapidly been progressed, because contamination of unnecessary substances such as chloride ion is unfavorable for such an infusion solution.

As a result of the present inventor's intensive study on L-cysteine derivatives which can stably be kept for a long period of time, it has now been found that the novel compound di-L-cysteine L-malate of the formula [I], i.e. a salt of 2 moles of L-cysteine with 1 mole of L-malic acid which is easily metabolized in vivo and has physiological activities such as improvement of liver function, shows excellent crystallizability and is extremely stable in the crystalline form.

The di-L-cysteine L-malate [I] of the present invention (hereinafter, referred to merely as "cysteine malate") is a novel crystalline substance and is useful for the preparation of amino acid infusion solutions or other medicines. Since L-malic acid has physiological activities such as improvement of liver function, the cysteine malate of the present invention shows not only the pharmacological activities owing to L-cysteine but also the activities owing to L-malic acid, and hence, it is very useful as a medicine.

The properties of the cysteine malate of the present invention are shown in the accompanying drawing.

Figure 1:
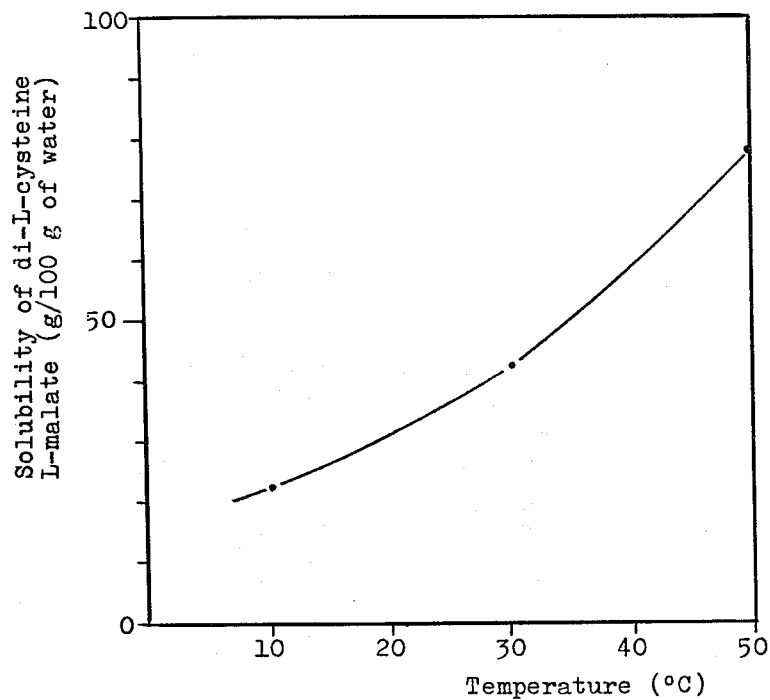
FIG. 1 shows a curve of solubility of cysteine malate in water.

The cysteine malate [I] of the present invention can be prepared by subjecting L-cysteine and L-malic acid to a neutralization reaction and recovering the resulting crystals.

The neutralization reaction can be carried out in an aqueous solvent, preferably water, wherein 2 moles of L-cysteine is preferably reacted with more than 0.9 mole, more preferably 1-2 moles, of L-malic acid. The starting L-cysteine and L-malic acid are used either in the free form or in the form of a salt with a mineral acid (e.g. hydrochloric acid) or an alkali metal (e.g. sodium). Since the L-cysteine is usually available in the form of a mineral acid salt (e.g. hydrochloride), it is preferable to use L-cysteine in the form of a mineral acid salt and L-malic acid in the free form in the neutralization reaction. When a L-cysteine mineral acid salt (e.g. hydrochloride) is used, the neutralization reaction is preferably carried out in the presence of an alkali metal hydroxide (e.g. sodium hydroxide, potassium hydroxide). The alkali metal hydroxide is usually used in an amount of 1 to 2 moles to 1 mole of L-malic acid. In this reaction, cysteine malate and an alkali metal salt (e.g. an alkali metal chloride) are produced in the reaction mixture. The reaction of a L-cysteine mineral acid salt (e.g. hydrochloride) and L-malic acid may be carried out by using an anion exchange resin. This process is usually carried out by intruducing an L-malic acid-containing aqueous solution into a column packed with an anion exchange resin (OH type) to absorb L-malic acid onto the resin and then intruducing thereto an aqueous solution containing an L-cysteine mineral acid salt (e.g. hydrochloride), whereby malic acid ion adsorbed onto the resin and a mineral acid ion (in case of hydrochloride, chloride ion) are mutually exchanged and the produced cysteine malate flow out through the column in the form of an effluent.

The cysteine malate produced by the above neutralization reaction can be crystallized as a highly pure crystal by conventional crystallization methods, for example, (1) a direct crystallization, i.e. by allowing to stand the reaction mixture in the presence or absence of the seed crystals, (2) by adding a hydrophilic organic solvent to the reaction mixture, or (3) by adding the reaction mixture to a hydrophilic organic solvent, among which the methods (1) or (2) are preferable because of simple operation.

In order to obtain the crystalline cysteine malate by the crystallization method (1), the reaction mixture is allowed to precipitate the crystals with adding the seed crystals or spontaneously without adding the seed crystals to the reaction mixture. This method is preferably carried out by regulating previously the concentration of cysteine malate in the reaction mixture within the range of about 30 to 80%, particularly about 40 to 70% by weight, by dilution or concentration (e.g. evaporation in vacuo) of the mixture, by which uniform crystals of the cysteine malate can be obtained. When the seed crystals is used, it is added in an amount of about 0.05% by weight based on the total amount of cysteine malate contained in the reaction mixture. The crystallization procedure may preferably be carried out by allowing to stand or stirring the mixture at a temperature of about 0° to 30° C.

The crystallization of cysteine malate by the method (2) can be carried out by adding a hydrophilic organic solvent to the reaction mixture. In this method, it is preferable, as like as in the above method (1), to regulate previously the concentration of cysteine malate in the mixture within the range of about 20 to 80%, more preferably particularly 30 to 70% by weight, by dilution or concentration of the reaction mixture, by which less amount of the organic solvent can be used and further the precipitated crystals do not become block-like. The organic solvent includes, for example, lower alkanols such as methanol, ethanol or isopropanol; di(lower)alkyl ketones such as acetone or methyl ethyl ketone; N,N'-dimethylformamide, or the like, which may be used alone or in combination of two or more thereof. These organic solvent may be used in somewhat different amounts depending on the kinds of the solvent, but they are usually used in such an amount that the water content of the solvent in the system becomes in the range of about 10 to 80%, particularly 30 to 70% by weight. The crystallization procedure can preferably be carried out by allowing to stand or stirring the mixture at a temperature of 0° to 30° C.

The crystallization of cysteine malate by the method (3) can be carried out by adding the reaction mixture to an appropriate amount of a hydrophilic organic solvent. In this method, it is also preferable, as like as in the above methods (1) and (2), to regulate previously the concentration of cysteine malate in the reaction mixture within the range of about 20 to 80%, particularly 30 to 70% by weight. The organic solvent includes the same solvents as used in the above method (2) and can be used in such as amount that the water content of the solvent after adding the reaction mixture becomes in a similar range to that in the above method (2), while the suitable amount may be somewhat different depending on the kinds of the solvent, likewise. The crystallization procedure can preferably be done by allowing to stand or stirring the reaction mixture at a temperature of 0° to 30° C.

The precipitated crystals of malate [I] obtained in the above methods can easily be separated from the system by conventional methods such as centrifugation or filtration.

The present invention is illustrated by the following Examples but is not limited thereto.

EXAMPLE 1

To an aqueous solution of free L-cysteine (1200 ml, content of L-cysteine: 0.653 mole is added L-malic acid (0.470 mole). After the mixture is reacted, the reaction mixture is concentrated under reduced pressure so as to regulate the total amount to 264 g.

The resulting aqueous solution is kept at 10° C. overnight to crystallize sufficiently. The precipitated crystals are collected by filtration and air-dried at 50° C. overnight to give crystalline di-L-cysteine L-malate (100.5 g, yield: 81.8%).

The crystalline product thus obtained is novel and has physicochemical properties as shown in Table 1.

TABLE 1

Figure 2:
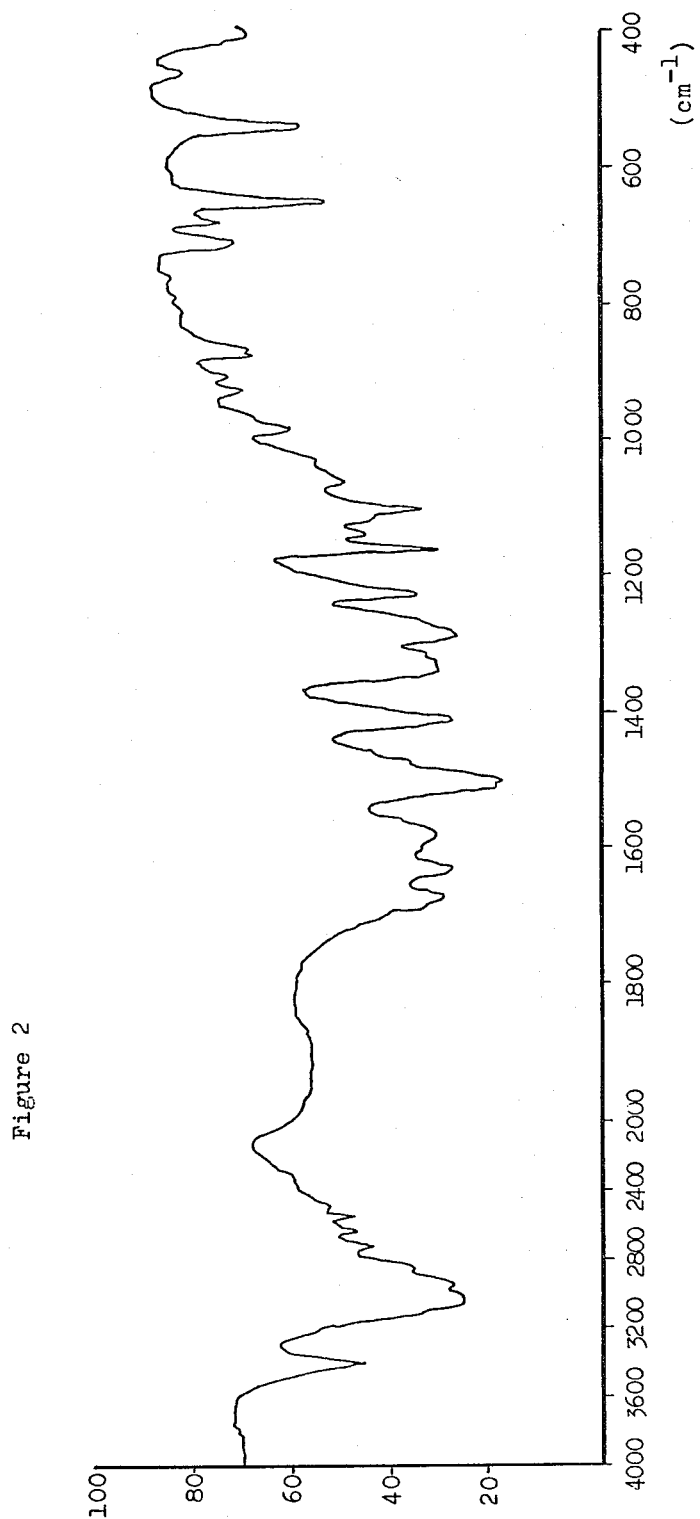
FIG. 2 shows an infrared spectrum (KBr method) of cysteine malate.

| Molecular formula | $(C_3H_7NSO_2)_2 \cdot C_4H_6O_5$ |
|---|---|
| Molecular weight | 376.4 |
| Appearance of crystals | Colorless, needles |
| Melting point | 164° C. (decomp.) |
| $[\alpha]_D^{20}$ (C = 8, N—HCl) | +5.87° |
| Solubility (g/100 g of water) | 22.2 (10° C.) |
| Curve of solubility in water | as shown in the accompanying FIG. 1 |
| Infrared spectrum (KBr method) | as shown in the accompanying FIG. 2 |

Elementary analysis for $(C_3H_7NSO_2)_2 \cdot C_4H_6O_5$: Calcd. (%): C,31.91; H,5.36; N,7.44; S,17.04 O,38.26. Found (%): C,32.08; H,5.41; N,7.41; S,17.02; O,38.12.

The content of L-cysteine of the above crystalline product is measured by spectrophotometry using 5,5'-dithio-bis(2-nitrobenzoic acid) reagent, and also the content of L-malic acid of the crystalline product is measured by spectrophotometry using 2,7-naphthalenediol reagent. The results are shown in Table 2.

TABLE 2

|  | Found (%) | Calculated (%) |
|---|---|---|
| L-Cysteine | 64.5 | 64.4 |

TABLE 2-continued

|  | Found (%) | Calculated (%) |
|---|---|---|
| L-malic acid | 35.8 | 35.6 |

Based on data of the above elementary analysis and contents of L-cysteine and L-malic acid, it is confirmed that the crystalline product obtained above is di-L-cysteine L-malate consisting of 2 moles of L-cysteine and 1 mole of L-malic acid.

Figure 3:
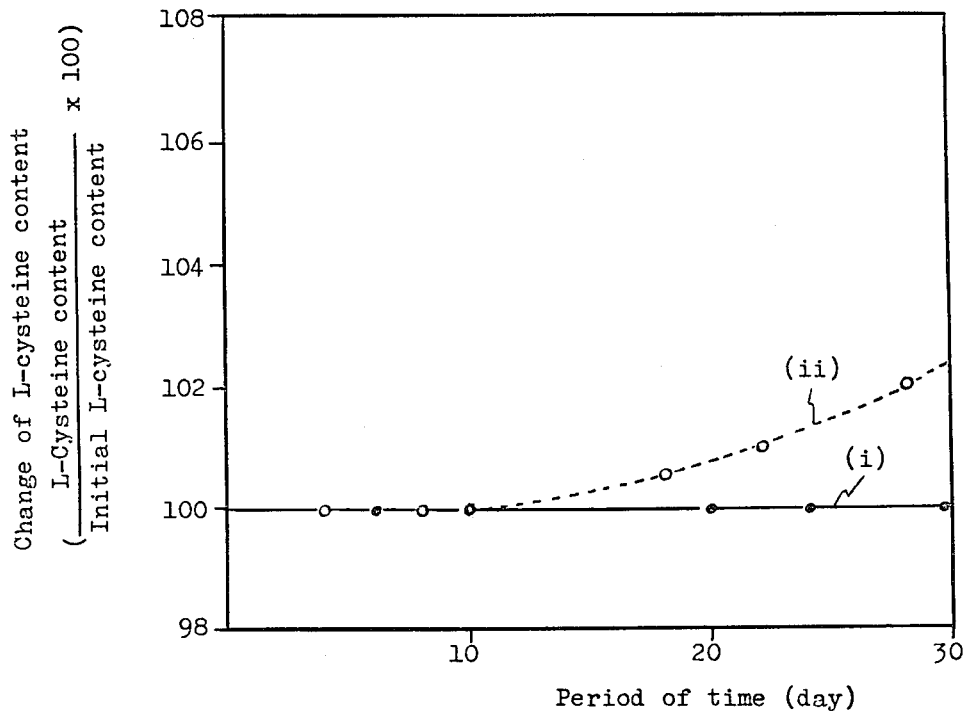
FIG. 3 shows curves of storage stability of cysteine malate (i) and L-cysteine hydrochloride anhydride (ii) when they are kept at 40° C.

The storage stability of the above crystalline product and L-cysteine hydrochloride anhydride is measured by keeping them at 40° C. The results are shown in the accompanying FIG. 3. From the data, it is confirmed that the above crystalline product has an excellent stability.

EXAMPLE 2

An aqueous solution of L-malic acid (1200 ml, content of L-malic acid: 0.60 mole) is introduced into a column packed with a weak basic ion exchange resin (Diaion WA-10 (OH type), 600 ml) and thereby L-malic acid is adsorbed onto the resin. A solution of crystalline L-cysteine hydrochloride monohydrate (120 g, 0.683 mole) in water (1000 ml) is introduced into the above column and thereby there is obtained an aqueous solution of L-cysteine L-malate as an effluent. The aqueous solution (containing L-cysteine: 0.642 mole and L-malic acid: 0.439 mole is concentrated under reduced pressure so as to regulate the total amount to 256 g. To the resulting solution is added isopropyl alcohol (100 ml), and the mixture is allowed to stand at 10° C. in order to precipitate crystals well. The precipitated crystals are collected by filtration and air-dried at 50° C. overnight to give crystalline di-L-cysteine L-malate (106.1 g, yield: 82.5%).

The physiocochemical properties of the crystalline product obtained above are identical to those of the product in Example 1.

EXAMPLE 3

L-Cysteine hydrochloride monohydrate (20 g), L-malic acid (7.63 g) and sodium hydroxide (4.55 g) are dissolved in water (100 ml), and the mixture is reacted. The resulting aqueous solution is concentrated under reduced pressure until the total amount becomes 57 g, and the solution is allowed to stand at 10° C. overnight. The precipitated crystals are collected by filtration, washed with aqueous isopropyl alcohol and air-dried at 50° C. to give crystalline di-L-cysteine L-malate (14.4 g, yield: 67.2%).

The physicochemical properties of the crystalline product obtained above are identical to those of the product in Example 1.

The contents of L-cysteine and L-malic acid of the above crystalline product are measured likewise. The results are shown in Table 3.

TABLE 3

|  | Found (%) | Calculated (%) |
|---|---|---|
| L-Cysteine | 65.1 | 64.4 |
| L-malic acid | 35.7 | 35.6 |

What is claimed is:
1. Di-L-cysteine L-malate of the formula:

[HS—CH$_2$—CH(NH$_3$)$^+$—COOH]$_2$·($^-$OOC—CHOH—CH$_2$—COO$^-$)

2. A process for the preparation of di-L-cysteine L-malate which comprises reacting 2 mole of L-cysteine mineral acid salt with more than 0.9 mole of L-malic acid in the presence of an alkali metal hydroxide and collecting the resulting crystalline di-L-cysteine L-malate.

3. A process according to claim 2, wherein the reaction of L-cysteine and L-malic acid is carried out by introducing an aqueous solution of L-malic acid into a column packed with an anion exchange resin and introducing thereto an aqueous solution of an L-cysteine mineral acid salt.

4. A process according to any one of claim 2, or 3, wherein the collection of crystalline di-L-cysteine L-malate is carried out by regulating the concentration of di-L-cysteine L-malate in the reaction mixture within the range of about 30 to 80% by weight, allowing to stand or stirring the mixture at a temperature of about 0° to 30° C. and then collecting the precipitated crystals.

5. A process according to claim 4, wherein a seed crystal of di-L-cysteine L-malate is added to the reaction mixture after the regulation of the concentration of di-L-cysteine L-malate.

6. A process according to claim 2 or 3, wherein the collection of crystalline di-L-cysteine L-malate is carried out by regulating the concentration of di-L-cysteine L-malate in the reaction mixture within the range of about 20 to 80% by weight, adding thereto a hydrophilic organic solvent in such an amount that the water content of the solvent in the system becomes in the range of about 10 to 80% by weight, allowing to stand or stirring the mixture at a temperature of 0° to 30° C., and collecting the precipitated crystals.

7. A process according to claim 6, wherein the hydrophilic organic solvent is a member selected from the group consisting of methanol, ethanol, isopropanol, acetone, methyl ethyl ketone, and N,N'-dimethylformamide.

8. A process according to claim 2 or 3, wherein the collection of crystalline di-L-cysteine L-malate is carried out by regulating the concentration of di-L-cysteine L-malate in the reaction mixture within the range of about 20 to 80% by weight, adding the resulting mixture to a hydrophilic organic solvent so that the water content of the solvent in the system becomes in the range of about 10 to 80% by weight, allowing to stand or stirring the mixture at a temperature of 0° to 30° C., and collecting the precipitated crystals.

9. A process according to claim 8, wherein the hydrophilic organic solvent is a member selected from the group consisting of methanol, ethanol, isopropanol, acetone, methyl ethyl ketone, and N,N'-dimethylformamide.

* * * * *